(12) United States Patent
Doyle et al.

(10) Patent No.: US 12,343,457 B2
(45) Date of Patent: Jul. 1, 2025

(54) DEVICE FOR DIFFUSING VOLATILE SUBSTANCES

(71) Applicant: ZOBELE HOLDING SPA, Trento (IT)

(72) Inventors: Dominic Doyle, Barcelona (ES); Sergio Luque Vera, Barcelona (ES); Fernando Alfonso Gallego, Barcelona (ES)

(73) Assignee: Zobele Holding, S.p.A, Trento (IT)

( * ) Notice: Subject to any disclaimer, the term of this patent is extended or adjusted under 35 U.S.C. 154(b) by 477 days.

(21) Appl. No.: 17/789,254

(22) PCT Filed: Dec. 28, 2020

(86) PCT No.: PCT/EP2020/087919
§ 371 (c)(1),
(2) Date: Jun. 27, 2022

(87) PCT Pub. No.: WO2021/130387
PCT Pub. Date: Jul. 1, 2021

(65) Prior Publication Data
US 2023/0034948 A1    Feb. 2, 2023

(30) Foreign Application Priority Data
Dec. 27, 2019   (ES) ............................... ES201931160

(51) Int. Cl.
*A61L 9/14* (2006.01)
*B05B 17/06* (2006.01)

(52) U.S. Cl.
CPC ............ *A61L 9/14* (2013.01); *B05B 17/0607* (2013.01); *A61L 2209/134* (2013.01)

(58) Field of Classification Search
None
See application file for complete search history.

(56) References Cited

U.S. PATENT DOCUMENTS

| 10,029,274 B1 | 7/2018 | Bumgartner et al. |
| 2007/0053789 A1* | 3/2007 | Ricciardi ............ B05B 17/0615 422/28 |
| 2015/0082689 A1 | 3/2015 | Bertrand et al. |

FOREIGN PATENT DOCUMENTS

| DE | 10234768 | 2/2004 |
| FR | 2787352 | 6/2000 |

(Continued)

OTHER PUBLICATIONS

International Search Report and the Written Opinion Dated May 6, 2021 From the International Searching Authority Re. Application No. PCT/EP2020/087919. (9 Pages).

*Primary Examiner* — Jelitza M Perez

(57) ABSTRACT

The device for diffusing volatile substances comprises a container (1) for housing a liquid containing the volatile substances and comprising an outlet for volatile substances (2) and an air inlet (3), and a nebulizer (5) with which the volatile substances are diffused to the outside, wherein the device for diffusing volatile substances also comprises a dispenser (4) that connects the volatile substances outlet (2) and the air inlet (3) to the nebulizer (5); a chamber (6) in which a mist of volatile substances is generated from the nebulizer (5), the chamber comprising an outlet hole (8) through which the mist of volatile substances exits.
It makes it possible to provide a device for releasing volatile substances in which no gas is necessary, natural fragrances can be used and with which good control of the dosage can be achieved.

7 Claims, 2 Drawing Sheets

(56) References Cited

FOREIGN PATENT DOCUMENTS

Figure 1:
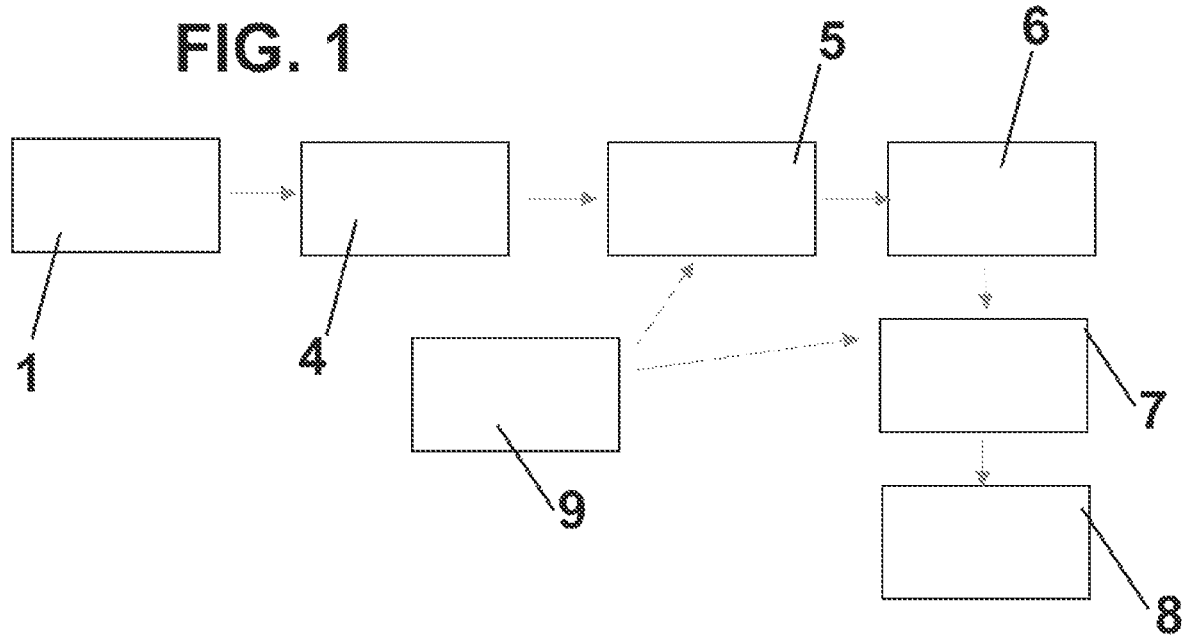
Figure 2:
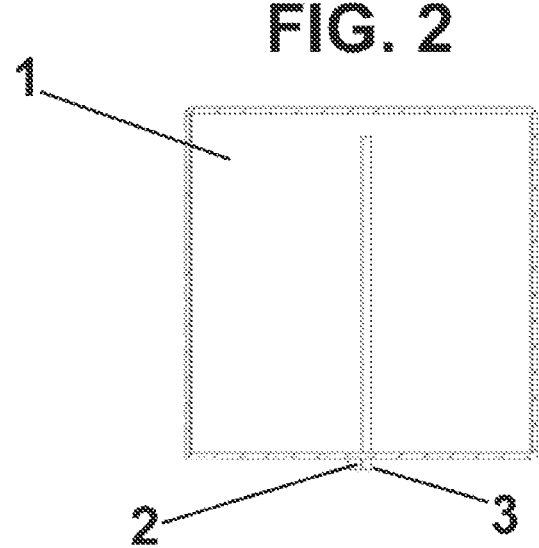
Figure 3:
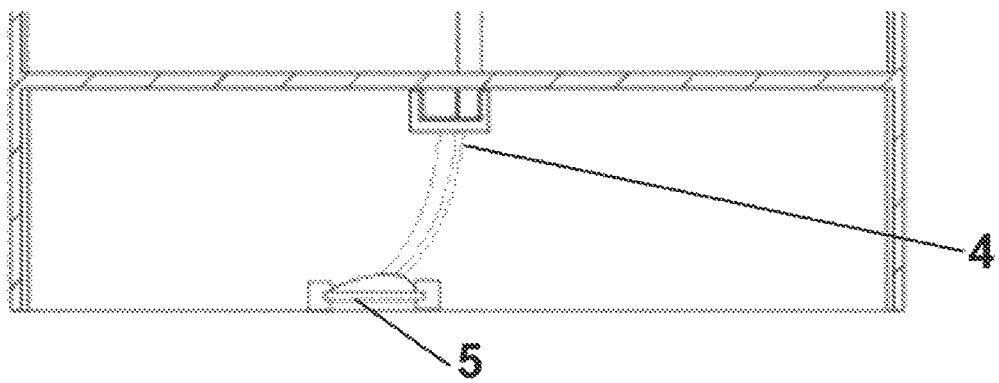
Figure 4:
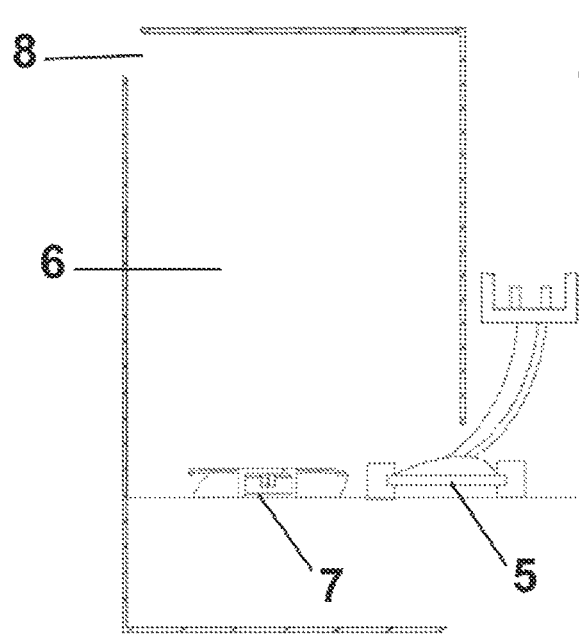
Figure 5:
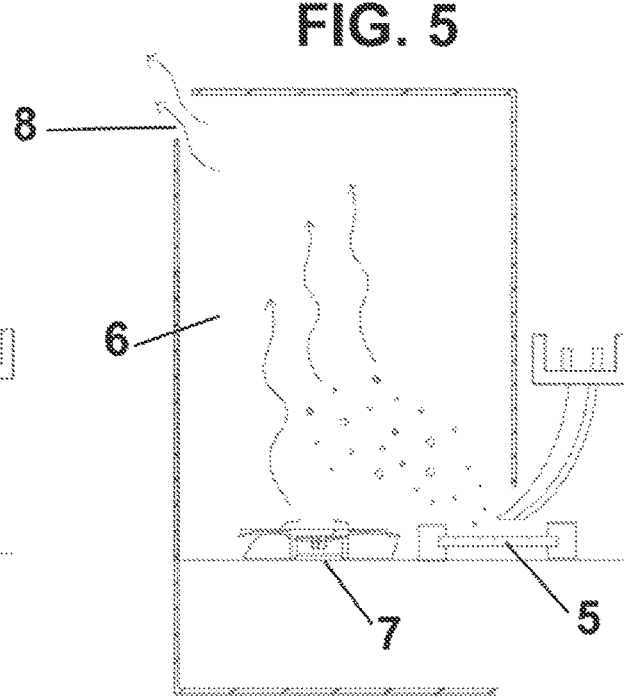

| GB | 2388062 | 3/2022 | |
|---|---|---|---|
| WO | WO 2012/127512 | 9/2012 | |
| WO | WO-2012127512 A1 * | 9/2012 | ......... B05B 17/0615 |

* cited by examiner

DEVICE FOR DIFFUSING VOLATILE SUBSTANCES

RELATED APPLICATIONS

This application is a National Phase of PCT Patent Application No. PCT/EP2020/087919 having International filing date of Dec. 28, 2020, which claims the benefit of priority of Spain Patent Application No. P201931160 filed on Dec. 27, 2019. The contents of the above applications are all incorporated by reference as if fully set forth herein in their entirety.

The present invention relates to a device for diffusing volatile substances.

FIELD AND BACKGROUND OF THE INVENTION

Electrical systems for the diffusion of volatile substances are known. Electric diffusers are devices for diffusing volatile substances with the use of energy that are used to activate elements such as fans, heaters, atomizers, nebulizers, aerosols in order to achieve optimal efficiency, optimal dose control and optimal control by the user on dispensing adjustment.

Some of these devices incorporate motors, heaters or solenoid valves that allow the vapors to escape through diffuser or dispenser systems such as nozzles and wicks. These devices are normally based on a container where the volatile substance is located, an electrical system for the evaporation of the volatile substance and a power system such as batteries or cells.

In other cases, the volatile substance is contained within a container in liquid form, and the electrical system is used to dispense the dose by heating to evaporation, by spraying, nebulization or other methods.

In other cases, this volatile substance is inside a pressurized metal housing, which acts as a protection and as a support, and which includes the propellant gas of the volatile substance that is intended to be diffused.

Currently existing solutions have different drawbacks.

In the case of nebulizers/atomizers, the volatile substances must contain different solvents, usually non-natural ones, to prevent the holes in the metal plate of the piezoelectric element from getting clogged.

In the case of diffusers that use a pressurized metal housing, the main problem they have is that they normally need a propellant gas for proper operation. In addition, the gas itself and the metal housing makes environmental sustainability not good There are other devices such as humidifiers or fragrance diffusers that use piezoelectric elements without a perforated metal plate, in which the problem is that the user adds the fragrance to the water manually, but there is no control regarding evaporation/dosage.

SUMMARY OF THE INVENTION

Therefore, the object of the present invention is to provide a device for releasing volatile substances in which no gas is necessary, natural, usually water-based, fragrances can be used, and with which we can have good control of the dosage.

With the device for diffusing volatile substances of the invention, the aforementioned drawbacks are solved, presenting other advantages that will be described below.

The device for diffusing volatile substances, comprising:

a container for housing a liquid containing the volatile substances and comprising an outlet for volatile substances and an air inlet, and a nebulizer with which volatile substances are diffused outside, wherein the device for diffusing volatile substances also includes:

a dispenser that connects the volatile substances outlet and the air inlet with the nebulizer;

a chamber in which a mist of volatile substances is generated from the nebulizer, the chamber comprising an outlet hole through which the mist of volatile substances exits.

The device for diffusing volatile substances according to the present invention also advantageously comprises an air stream generator in said chamber that directs the mist of volatile substances to the outlet hole.

Furthermore, the dispenser advantageously doses the liquid containing the volatile substances to the nebulizer drop by drop, and the air inlet is liquid-tight.

According to a preferred embodiment, the air stream generator is arranged at the bottom of the chamber, and the outlet port is arranged at the top of the chamber.

Preferably, said nebulizer is placed next to the air stream generator

The device for diffusing volatile substances according to the present invention also advantageously comprises electronic control means connected to the nebulizer and the air stream generator.

Said electronic control means, for example a processor, adjusts the evaporation level selected by the user and adjusts the force of expulsion of the mist of volatile substances.

As indicated above, the device for releasing volatile substances according to the present invention has, among others, the following advantages:

- no gas is necessary,
- allows the use of natural, usually water-based fragrances and
- allows having a good control of the dosage.

BRIEF DESCRIPTION OF THE SEVERAL VIEWS OF THE DRAWINGS

In order to better understand what has been stated, some drawings are attached in which, schematically and only as a non-limiting example, a practical case of embodiment is represented.

FIG. 1 is a block diagram of the components of the device for diffusing volatile substances according to the present invention;

FIG. 2 is a sectional elevation view of the volatile substances container of the device for diffusing volatile substances according to the present invention;

FIG. 3 is a sectional elevation view of a part of the device for diffusing volatile substances according to the present invention, wherein the dispenser and the nebulizer can be seen;

FIG. 4 is a sectional elevation view of the chamber of the device for diffusing volatile substances according to the present invention, when a drop has been formed on the nebulizer by the dispenser; and FIG. 5 is a sectional elevation view of the chamber of the device for diffusing volatile substances according to the present invention, when the mist of volatile substances is generated and diffuses through the outlet hole of the chamber.

DESCRIPTION OF SPECIFIC EMBODIMENTS OF THE INVENTION

As shown in the figures, the device for diffusing volatile substances according to the present invention comprises a container 1 for housing a liquid containing the volatile substances, said container 1 comprising an outlet 2 for the liquid containing the volatile substances and a air inlet 3, connecting or located in the part of the container where there is no liquid.

Said liquid outlet 2 and said air inlet 3 are preferably arranged in the lower part of said container 1, and said air inlet 3 is liquid-tight, that is, it does not allow the entry of liquid into the container 1.

The device for diffusing volatile substances also comprises a dispenser 4 that drops the liquid containing the volatile substances drop by drop through said liquid outlet 2.

The dispenser 4 doses said liquid drop by drop to a nebulizer 5, which is in charge of converting the drop of liquid into a mist of volatile substances. Said nebulizer 5 is conventional, for example, a piezoelectric element